US009113906B2

(12) United States Patent
Mueller

(10) Patent No.: US 9,113,906 B2
(45) Date of Patent: *Aug. 25, 2015

(54) COMPACT JAW INCLUDING SPLIT PIVOT PIN

(71) Applicant: COVIDIEN LP, Mansfield, MA (US)

(72) Inventor: Peter M. Mueller, Frederick, CO (US)

(73) Assignee: Covidien LP, Mansfield, MA (US)

( * ) Notice: Subject to any disclaimer, the term of this patent is extended or adjusted under 35 U.S.C. 154(b) by 190 days.

This patent is subject to a terminal disclaimer.

(21) Appl. No.: 13/933,409

(22) Filed: Jul. 2, 2013

(65) Prior Publication Data

US 2013/0296854 A1 Nov. 7, 2013

Related U.S. Application Data

(63) Continuation of application No. 12/692,414, filed on Jan. 22, 2010, now Pat. No. 8,480,671.

(51) Int. Cl.
A61B 17/28 (2006.01)
A61B 18/14 (2006.01)
(Continued)

(52) U.S. Cl.
CPC ..... *A61B 18/1445* (2013.01); *A61B 2017/2945* (2013.01); *A61B 2018/0063* (2013.01); *A61B 2018/00404* (2013.01); *A61B 2018/00601* (2013.01); *A61B 2018/1412* (2013.01);
(Continued)

(58) Field of Classification Search
CPC ............... A61B 2018/126; A61B 18/1442; A61B 18/1445; A61B 2018/1455
USPC ...................... 606/51, 52, 205, 207
See application file for complete search history.

(56) References Cited

U.S. PATENT DOCUMENTS

D249,549 S    9/1978  Pike
D263,020 S    2/1982  Rau, III
(Continued)

FOREIGN PATENT DOCUMENTS

CN    201299462    9/2009
DE      2416253   10/1975
(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
(Continued)

Primary Examiner — Joseph Stoklosa
Assistant Examiner — Jocelyn D Ram

(57) ABSTRACT

An end effector assembly for use with a forceps includes a pair of jaw members, a knife assembly, and one or more cam assemblies. One or more of the jaw members are moveable relative to the other about a pivot between open and closed positions. One or more of the jaw members include a knife channel. The pivot includes first and second sections defining a passage therebetween. The knife assembly includes a knife blade and an actuation shaft. The knife blade is disposed distally relative to the pivot. The actuation shaft is configured for slidable translation through the passage to allow selective advancement of the knife blade through the knife channel. The one or more cam assemblies are operably coupled to the one or more moveable jaw members and are actuatable to move the one or more jaw members between the open and closed positions for grasping tissue therebetween.

10 Claims, 15 Drawing Sheets

(51) Int. Cl.
   *A61B 17/29* (2006.01)
   *A61B 18/00* (2006.01)
   *A61B 18/18* (2006.01)

(52) U.S. Cl.
   CPC . *A61B2018/1432* (2013.01); *A61B 2018/1455* (2013.01); *A61B 2018/1861* (2013.01)

(56) References Cited

U.S. PATENT DOCUMENTS

| Number | Type | Date | Name | Ref |
|---|---|---|---|---|
| D295,893 | S | 5/1988 | Sharkany et al. | |
| D295,894 | S | 5/1988 | Sharkany et al. | |
| D298,353 | S | 11/1988 | Manno | |
| D299,413 | S | 1/1989 | DeCarolis | |
| D343,453 | S | 1/1994 | Noda | |
| D348,930 | S | 7/1994 | Olson | |
| D349,341 | S | 8/1994 | Lichtman et al. | |
| D354,564 | S | 1/1995 | Medema | |
| D358,887 | S | 5/1995 | Feinberg | |
| 5,496,317 | A * | 3/1996 | Goble et al. | 606/48 |
| 5,496,347 | A | 3/1996 | Hashiguchi et al. | |
| 5,540,685 | A | 7/1996 | Parins et al. | |
| D384,413 | S | 9/1997 | Zlock et al. | |
| H1745 | H | 8/1998 | Paraschac | |
| D402,028 | S | 12/1998 | Grimm et al. | |
| D408,018 | S | 4/1999 | McNaughton | |
| D416,089 | S | 11/1999 | Barton et al. | |
| D424,694 | S | 5/2000 | Tetzlaff et al. | |
| D425,201 | S | 5/2000 | Tetzlaff et al. | |
| H1904 | H | 10/2000 | Yates et al. | |
| D449,886 | S | 10/2001 | Tetzlaff et al. | |
| D453,923 | S | 2/2002 | Olson | |
| D454,951 | S | 3/2002 | Bon | |
| D457,958 | S | 5/2002 | Dycus et al. | |
| D457,959 | S | 5/2002 | Tetzlaff et al. | |
| H2037 | H | 7/2002 | Yates et al. | |
| D465,281 | S | 11/2002 | Lang | |
| D466,209 | S | 11/2002 | Bon | |
| D493,888 | S | 8/2004 | Reschke | |
| D496,997 | S | 10/2004 | Dycus et al. | |
| D499,181 | S | 11/2004 | Dycus et al. | |
| D502,994 | S | 3/2005 | Blake, III | |
| D509,297 | S | 9/2005 | Wells | |
| D525,361 | S | 7/2006 | Hushka | |
| 7,083,618 | B2 * | 8/2006 | Couture et al. | 606/51 |
| 7,101,371 | B2 | 9/2006 | Dycus et al. | |
| D531,311 | S | 10/2006 | Guerra et al. | |
| D533,274 | S | 12/2006 | Visconti et al. | |
| D533,942 | S | 12/2006 | Kerr et al. | |
| 7,150,097 | B2 | 12/2006 | Sremcich et al. | |
| 7,150,749 | B2 | 12/2006 | Dycus et al. | |
| D535,027 | S | 1/2007 | James et al. | |
| 7,156,846 | B2 | 1/2007 | Dycus et al. | |
| D538,932 | S | 3/2007 | Malik | |
| D541,418 | S | 4/2007 | Schechter et al. | |
| D541,611 | S | 5/2007 | Aglassinge | |
| D541,938 | S | 5/2007 | Kerr et al | |
| D545,432 | S | 6/2007 | Watanabe | |
| D547,154 | S | 7/2007 | Lee | |
| 7,252,667 | B2 | 8/2007 | Moses et al. | |
| 7,255,697 | B2 | 8/2007 | Dycus et al. | |
| D564,662 | S | 3/2008 | Moses et al. | |
| D567,943 | S | 4/2008 | Moses et al. | |
| D575,395 | S | 8/2008 | Hushka | |
| D575,401 | S | 8/2008 | Hixson et al. | |
| 7,442,194 | B2 | 10/2008 | Dumbauld et al. | |
| 7,445,621 | B2 | 11/2008 | Dumbauld et al. | |
| D582,038 | S | 12/2008 | Swoyer et al. | |
| 7,481,810 | B2 | 1/2009 | Dumbauld et al. | |
| 7,491,201 | B2 * | 2/2009 | Shields et al. | 606/51 |
| 7,500,975 | B2 | 3/2009 | Cunningham et al. | |
| 7,540,872 | B2 | 6/2009 | Schechter et al. | |
| D617,900 | S | 6/2010 | Kingsley et al. | |
| D617,901 | S | 6/2010 | Unger et al. | |
| D617,902 | S | 6/2010 | Twomey et al. | |
| D617,903 | S | 6/2010 | Unger et al. | |
| D618,798 | S | 6/2010 | Olson et al. | |
| D621,503 | S | 8/2010 | Otten et al. | |
| D627,462 | S | 11/2010 | Kingsley | |
| D628,289 | S | 11/2010 | Romero | |
| D628,290 | S | 11/2010 | Romero | |
| D630,324 | S | 1/2011 | Reschke | |
| 7,887,536 | B2 | 2/2011 | Johnson et al. | |
| 7,935,130 | B2 * | 5/2011 | Williams | 606/208 |
| 7,951,150 | B2 | 5/2011 | Johnson et al. | |
| 8,016,827 | B2 | 9/2011 | Chojin | |
| D649,249 | S | 11/2011 | Guerra | |
| D649,643 | S | 11/2011 | Allen, IV et al. | |
| 8,112,871 | B2 | 2/2012 | Brandt et al. | |
| 8,114,122 | B2 | 2/2012 | Nau, Jr. | |
| 8,133,254 | B2 | 3/2012 | Dumbauld et al. | |
| 8,142,473 | B2 | 3/2012 | Cunningham | |
| 8,162,965 | B2 | 4/2012 | Reschke et al. | |
| 8,162,973 | B2 | 4/2012 | Cunningham | |
| 8,187,273 | B2 | 5/2012 | Kerr et al. | |
| D661,394 | S | 6/2012 | Romero et al. | |
| 8,197,479 | B2 | 6/2012 | Olson et al. | |
| 8,226,650 | B2 | 7/2012 | Kerr | |
| 8,246,618 | B2 * | 8/2012 | Bucciaglia et al. | 606/51 |
| 8,251,994 | B2 | 8/2012 | McKenna et al. | |
| 8,257,387 | B2 | 9/2012 | Cunningham | |
| 8,266,783 | B2 | 9/2012 | Brandt et al. | |
| 8,480,671 | B2 * | 7/2013 | Mueller | 606/51 |
| 2002/0115997 | A1 | 8/2002 | Truckai et al. | |
| 2003/0018331 | A1 | 1/2003 | Dycus et al. | |
| 2003/0229344 | A1 | 12/2003 | Dycus et al. | |
| 2004/0122423 | A1 * | 6/2004 | Dycus et al. | 606/51 |
| 2005/0096651 | A1 | 5/2005 | Truckai et al. | |
| 2006/0064085 | A1 * | 3/2006 | Schechter et al. | 606/50 |
| 2006/0074417 | A1 | 4/2006 | Cunningham et al. | |
| 2006/0084973 | A1 | 4/2006 | Hushka | |
| 2006/0129146 | A1 | 6/2006 | Dycus et al. | |
| 2007/0043352 | A1 | 2/2007 | Garrison et al. | |
| 2007/0043353 | A1 | 2/2007 | Dycus et al. | |
| 2007/0062017 | A1 | 3/2007 | Dycus et al. | |
| 2007/0078458 | A1 | 4/2007 | Dumbauld et al. | |
| 2007/0088356 | A1 | 4/2007 | Moses et al. | |
| 2007/0142833 | A1 | 6/2007 | Dycus et al. | |
| 2007/0173814 | A1 | 7/2007 | Hixson et al. | |
| 2007/0179499 | A1 | 8/2007 | Garrison | |
| 2008/0015566 | A1 * | 1/2008 | Livneh | 606/37 |
| 2008/0319442 | A1 | 12/2008 | Unger et al. | |
| 2009/0012520 | A1 | 1/2009 | Hixson et al. | |
| 2009/0138006 | A1 | 5/2009 | Bales et al. | |
| 2009/0149854 | A1 | 6/2009 | Cunningham et al. | |
| 2009/0182327 | A1 * | 7/2009 | Unger | 606/46 |
| 2010/0016857 | A1 | 1/2010 | Mckenna et al. | |
| 2010/0023009 | A1 | 1/2010 | Moses et al. | |
| 2010/0036375 | A1 | 2/2010 | Regadas | |
| 2010/0042143 | A1 | 2/2010 | Cunningham | |
| 2010/0049187 | A1 | 2/2010 | Carlton et al. | |
| 2010/0057081 | A1 | 3/2010 | Hanna | |
| 2010/0057082 | A1 | 3/2010 | Hanna | |
| 2010/0057083 | A1 | 3/2010 | Hanna | |
| 2010/0057084 | A1 | 3/2010 | Hanna | |
| 2010/0063500 | A1 | 3/2010 | Muszala | |
| 2010/0069903 | A1 | 3/2010 | Allen, IV et al. | |
| 2010/0069904 | A1 | 3/2010 | Cunningham | |
| 2010/0069953 | A1 | 3/2010 | Cunningham | |
| 2010/0076427 | A1 | 3/2010 | Heard | |
| 2010/0076430 | A1 | 3/2010 | Romero | |
| 2010/0076431 | A1 | 3/2010 | Allen, IV | |
| 2010/0076432 | A1 | 3/2010 | Horner | |
| 2010/0087816 | A1 | 4/2010 | Roy | |
| 2010/0094271 | A1 | 4/2010 | Ward et al. | |
| 2010/0094287 | A1 | 4/2010 | Cunningham et al. | |
| 2010/0100122 | A1 | 4/2010 | Hinton | |
| 2010/0130971 | A1 | 5/2010 | Baily | |
| 2010/0130977 | A1 | 5/2010 | Garrison et al. | |
| 2010/0145334 | A1 * | 6/2010 | Olson et al. | 606/48 |
| 2010/0179543 | A1 | 7/2010 | Johnson et al. | |
| 2010/0179545 | A1 | 7/2010 | Twomey et al. | |
| 2010/0179546 | A1 | 7/2010 | Cunningham | |
| 2010/0179547 | A1 | 7/2010 | Cunningham et al. | |

(56) References Cited

U.S. PATENT DOCUMENTS

| | | |
|---|---|---|
| 2010/0249769 A1 | 9/2010 | Nau, Jr. et al. |
| 2010/0274244 A1 | 10/2010 | Heard |
| 2010/0280511 A1 | 11/2010 | Rachlin et al. |
| 2010/0280515 A1 | 11/2010 | Hixson et al. |
| 2011/0015632 A1 | 1/2011 | Artale |
| 2011/0034918 A1 | 2/2011 | Reschke |
| 2011/0046623 A1 | 2/2011 | Reschke |
| 2011/0054467 A1 | 3/2011 | Mueller et al. |
| 2011/0054468 A1 | 3/2011 | Dycus |
| 2011/0054469 A1 | 3/2011 | Kappus et al. |
| 2011/0054471 A1 | 3/2011 | Gerhardt et al. |
| 2011/0054472 A1 | 3/2011 | Romero |
| 2011/0060333 A1* | 3/2011 | Mueller ................ 606/46 |
| 2011/0060334 A1 | 3/2011 | Brandt et al. |
| 2011/0060335 A1 | 3/2011 | Harper et al. |
| 2011/0071523 A1 | 3/2011 | Dickhans |
| 2011/0077648 A1 | 3/2011 | Lee et al. |
| 2011/0077649 A1 | 3/2011 | Kingsley |
| 2011/0082457 A1 | 4/2011 | Kerr et al. |
| 2011/0082494 A1 | 4/2011 | Kerr et al. |
| 2011/0087221 A1 | 4/2011 | Siebrecht et al. |
| 2011/0098689 A1 | 4/2011 | Nau, Jr. et al. |
| 2011/0118736 A1 | 5/2011 | Harper et al. |
| 2011/0184405 A1 | 7/2011 | Mueller |
| 2011/0190653 A1 | 8/2011 | Harper et al. |
| 2011/0190765 A1 | 8/2011 | Chojin |
| 2011/0193608 A1 | 8/2011 | Krapohl |
| 2011/0218530 A1 | 9/2011 | Reschke |
| 2011/0230880 A1 | 9/2011 | Chojin et al. |
| 2011/0238066 A1 | 9/2011 | Olson |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009 165 | 6/2007 |
| DE | 20 2007 009318 | 8/2007 |
| DE | 20 2007 00931 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 1 486 177 | 12/2004 |
| EP | 1 535 581 | 6/2005 |
| EP | 1281878 | 10/2005 |
| EP | 1 642 543 | 4/2006 |
| EP | 1 649 821 | 4/2006 |
| EP | 1 810 625 | 7/2007 |
| EP | 2243439 | 10/2010 |
| EP | 2294998 | 3/2011 |
| JP | 61-501068 | 9/1984 |
| JP | 65-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-511401 | 12/1994 |
| JP | 06343644 | 12/1994 |
| JP | 07265328 | 10/1995 |
| JP | 8-317936 | 3/1996 |
| JP | 08056955 | 3/1996 |
| JP | 8-289895 | 5/1996 |
| JP | 08252263 | 10/1996 |
| JP | 8-317934 | 12/1996 |
| JP | 9-000538 | 1/1997 |
| JP | 09010223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47149 | 2/1999 |
| JP | 11-47150 | 2/1999 |
| JP | 11-169381 | 6/1999 |
| JP | 11-192238 | 7/1999 |
| JP | 11244298 | 9/1999 |
| JP | 2000-135222 | 5/2000 |
| JP | 2000-342599 | 12/2000 |
| JP | 2000-350732 | 12/2000 |
| JP | 2001-008944 | 1/2001 |
| JP | 2001-29355 | 2/2001 |
| JP | 2001-029356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 | 6/2005 |
| JP | 2005-253789 | 9/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/45589 | 6/2002 |
| WO | WO 2004/073490 | 9/2004 |
| WO | WO 2005/004734 | 1/2005 |
| WO | WO 2005/004735 | 1/2005 |
| WO | WO 2005/110264 | 11/2005 |
| WO | WO 2006021269 | 3/2006 |
| WO | WO 2008/008457 | 1/2008 |
| WO | WO 2008/040483 | 4/2008 |
| WO | WO 2011/018154 | 2/2011 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Tinkeler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

(56) References Cited

OTHER PUBLICATIONS

E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; 16 Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. I Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4. Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan, 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.

(56) References Cited

OTHER PUBLICATIONS

Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan, 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCI/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No. 11151509 dated Jun. 6, 2011.
International Search Report corresponding to European Application No. EP 10175956, dated Nov. 12, 2010.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 091591,328, filed Jun. 9, 2000, Thomas P. Ryan.
U.S. Appl. No. 12/336,970, filed Dec. 17, 2008, Paul R. Sremeich.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/868,732, filed Apr. 23, 2013, Mueller.
U.S. Appl. No. 13/893,527, filed May 14, 2013, Horner.
U.S. Appl. No. 13/903,091, filed May 28, 2013, Nau.
U.S. Appl. No. 13/903,116, filed May 28, 2013, Nau.
U.S. Appl. No. 13/903,223, filed May 28, 2013, Payne.
U.S. Appl. No. 13/909,362, filed Jun. 4, 2013, Kerr.
U.S. Appl. No. 13/911,674, filed Jun. 6, 2013, Kerr.
U.S. Appl. No. 13/920,643, filed Jun. 18, 2013, Nau.
U.S. Appl. No. 13/922,377, filed Jun. 20, 2013, Allen.
U.S. Appl. No. 13/922,975, filed Jun. 20, 2013, McKenna.
U.S. Appl. No. 13/933,409, filed Jul. 2, 2013, Mueller.
U.S. Appl. No. 13/933,683, filed Jul. 2, 2013, Nau.
U.S. Appl. No. 13/936,510, filed Jul. 8, 2013, Kerr.
U.S. Appl. No. 13/947,991, filed Jul. 22, 2013, Kerr.
U.S. Appl. No. 13/969,204, filed Aug. 16, 2013, Bucciaglia.
U.S. Appl. No. 13/969,278, filed Aug. 16, 2013, Kerr.
U.S. Appl. No. 14/017,572, filed Sep. 4, 2013, Arya.
U.S. Appl. No. 14/019,031, filed Sep. 5, 2013, Garrison.
U.S. Appl. No. 14/019,094, filed Sep. 5, 2013, Garrison.

* cited by examiner

COMPACT JAW INCLUDING SPLIT PIVOT PIN

CROSS REFERENCE TO RELATED APPLICATIONS

This application is a continuation of U.S. patent application Ser. No. 12/692,414, filed on Jan. 22, 2010, now U.S. Pat. No. 8,480,671, the contents of which are incorporated herein in their entirety.

BACKGROUND

1. Technical Field

The present disclosure relates to an apparatus for performing an endoscopic electrosurgical procedure. More particularly, the present disclosure relates to an apparatus for performing an endoscopic electrosurgical procedure that employs an endoscopic electrosurgical apparatus that includes an end effector assembly configured for use with variously-sized access ports.

2. Description of Related Art

Electrosurgical apparatuses (e.g., electrosurgical forceps) are well known in the medical arts and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect homeostasis by heating the tissue and blood vessels to coagulate, cauterize, fuse, seal, cut, desiccate, and/or fulgurate tissue.

As an alternative to open electrosurgical forceps for use with open surgical procedures, many modern surgeons use endoscopes and endoscopic electrosurgical apparatus (e.g., endoscopic forceps) for remotely accessing organs through smaller, puncture-like incisions. As a direct result thereof, patients tend to benefit from less scarring, less pain, and reduced healing time. Typically, the endoscopic forceps are inserted into the patient through one or more various types of cannulas or access ports (typically having an opening that ranges from about five millimeters to about fifteen millimeters) that has been made with a trocar; as can be appreciated, smaller cannulas are usually preferred.

Endoscopic forceps that are configured for use with small cannulas (e.g., cannulas less than five millimeters) may present design challenges for a manufacturer of endoscopic instruments.

SUMMARY

Accordingly, an end effector assembly for use with a forceps includes a pair of jaw members, a knife assembly, and one or more cam assemblies. One or both of the jaw members are moveable relative to the other about a pivot between an open position and a closed position for grasping tissue. One or both of the jaw members include a knife channel defined therein that extends therealong. In embodiments, one or both jaw members are adapted to connect to an electrosurgical energy source to electrosurgically treat tissue. The pivot has first and second sections defining a passage therebetween.

The knife assembly includes a knife blade and an actuation shaft. The knife blade may be affixed to a distal end of the actuation shaft. The knife blade is disposed distally relative to the pivot. The actuation shaft is configured for slidable translation through the passage defined between the first and second sections of the pivot to allow selective advancement of the knife blade through the knife channel.

The one or more cam assemblies are operably coupled to the one or more moveable jaw members and are actuatable to move one or both jaw members between the open and the closed position for grasping tissue therebetween. The one or more cam assemblies include an actuator configured to move each movable jaw member between the open and the closed position upon selective longitudinal translation thereof. The actuator may be moveable to actuate both jaw members. The actuator includes one or more cam pins extending therefrom. One or both jaw members define one or more cam slots therein such that the one or more cam slots and the one or more cam pins are configured to cooperate with one another to move each moveable jaw member. An actuator tube is operably associated with the forceps which is configured to longitudinally translate the actuator and permit the slidable translation of the actuation shaft therethrough. In one embodiment, a roll joint is operably coupled to the actuator tube and is configured to facilitate rotational movement of the jaw members.

The end effector assembly includes a knife tube mounted to the pivot wherein the one or more cam pins are configured to slidably engage the knife tube upon the selective longitudinal translation of the actuator. The knife tube defines a recess adapted to mount each of the first and second sections of the pivot at the distal ends thereof. The distal ends of each of the first and second sections define a profile configured to engage the recess.

According to another aspect, a forceps includes a housing, a pair of jaw members, a knife assembly, and one or more cam assemblies. The housing has a shaft that extends therefrom that includes a clevis at a distal end thereof. The shaft of the housing includes an actuator tube.

The pair of jaw members are mounted to the clevis about a pivot. One or both jaw members are moveable relative to the other about the pivot between an open position and a closed position for grasping tissue. One or both of the jaw members include a knife channel defined therein that extends thereal-ong. One or both of the jaw members may be adapted to connect to an electrosurgical energy source to electrosurgically treat tissue. The pivot has first and second sections defining a passage therebetween. In embodiments, the first and second sections of the pivot are fixedly connected to the clevis.

The knife assembly includes a knife blade and an actuation shaft. The knife blade may be affixed to a distal end of the actuation shaft. The knife blade is disposed distally relative to the pivot. The actuation shaft is configured for slidable translation through the passage defined between the first and second sections of the pivot to allow selective advancement of the knife blade through the knife channel.

The one or more cam assemblies are operably coupled to each moveable jaw member and are actuatable to move one or both jaw members between the open and the closed position for grasping tissue therebetween. One or more cam assemblies include an actuator operably coupled to the housing that is configured to move one or both jaw members between the open and the closed position upon selective longitudinal translation thereof. The actuator may be moveable to actuate both jaw members. The actuator includes one or more cam pins extending therefrom. One or both jaw members define one or more cam slots therein such that the one or more cam slots and the one or more cam pins are configured to cooperate with one another to move each moveable jaw member. The actuator tube is configured to longitudinally translate the actuator and permit the slidable translation of the actuation shaft therethrough.

The forceps includes a knife tube mounted to the pivot. The one or more cam pins are configured to slidably engage the knife tube upon the selective longitudinal translation of the actuator. The knife tube defines a recess adapted to mount each of the first and second sections of the pivot at the distal ends thereof. The distal ends of each of the first and second sections define a profile configured to engage the recess.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Detailed embodiments of the present disclosure are disclosed herein; however, the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful in the arts to provide an electrosurgical apparatus that is suitable for use with various access ports, including but not limited to those that are greater than and/or less than five millimeters. With this purpose in mind, the present disclosure includes an electrosurgical forceps that includes a drive assembly operatively coupled to one or more jaw members associated with the end effector assembly of the electrosurgical forceps. The drive assembly is configured to move the jaw members from an open to a closed configuration such that when actuated, the jaw members form a closed loop electrical circuit such that a desired tissue effect (e.g., tissue seal) may be achieved.

Figure 1A:
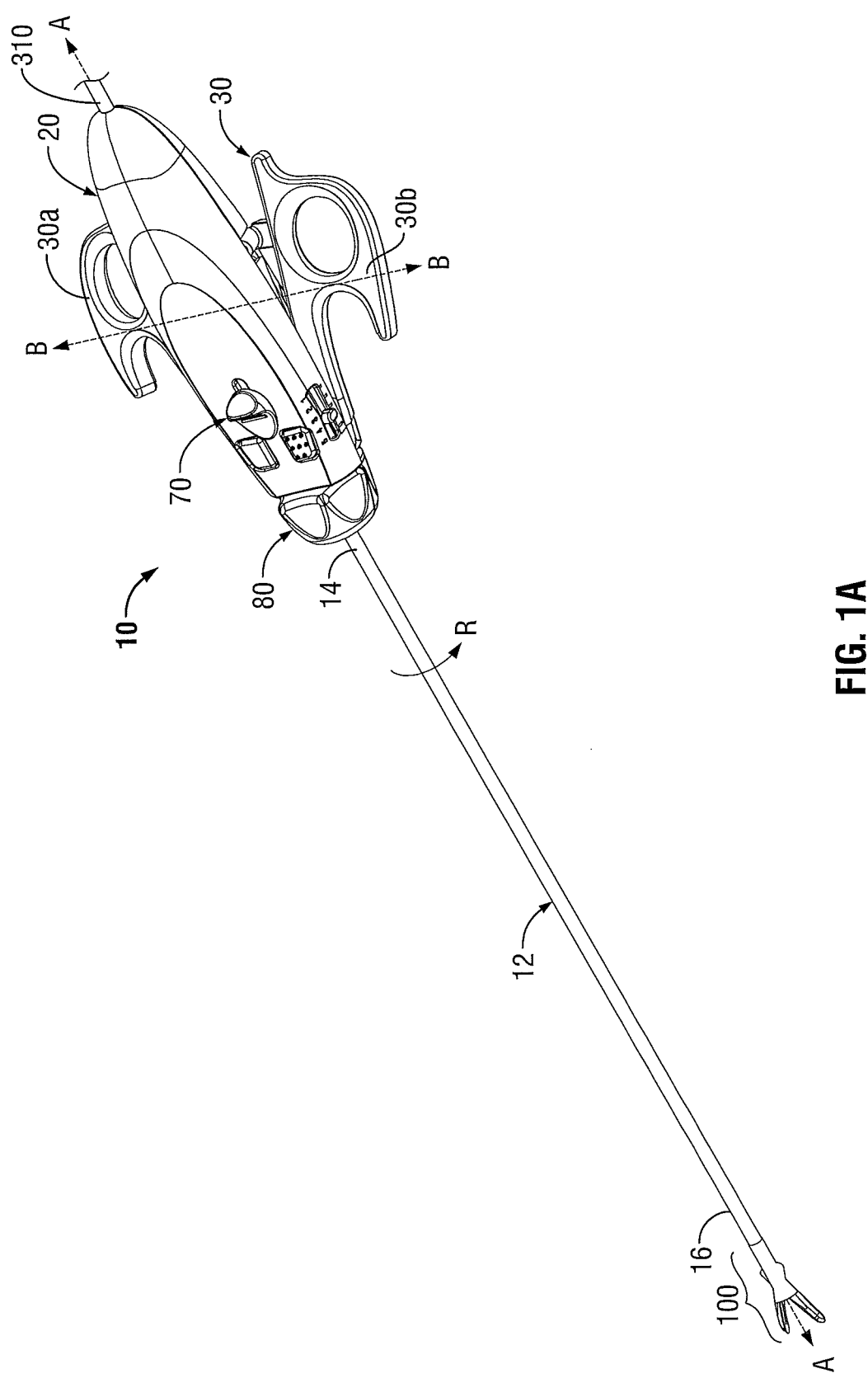
FIG. 1A is a top, perspective view of an endoscopic forceps shown in an open configuration and including a housing, a handle assembly, a shaft and an end effector assembly according to the present disclosure.
Figure 1B:
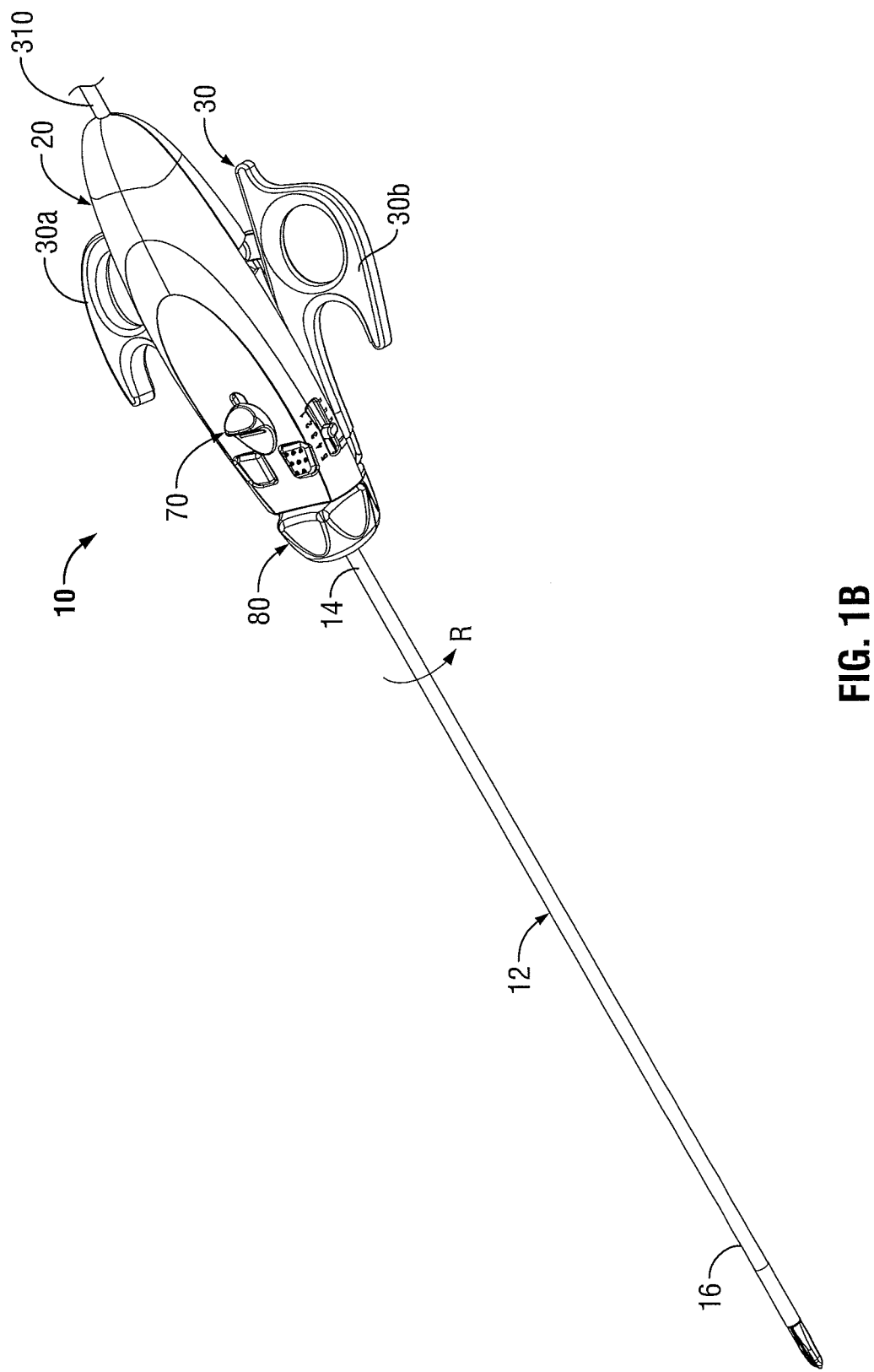
FIG. 1B is a top, perspective view of the endoscopic forceps of FIG. 1A showing the end effector assembly in a closed configuration according to the present disclosure.

Turning now to FIGS. 1A and 1B, one embodiment of an electrosurgical forceps 10 is shown for use with various surgical procedures and generally includes a housing 20, a handle assembly 30, a rotating assembly 80, a knife trigger assembly 70 and an end effector assembly 100 which mutually cooperate to grasp, seal and divide tubular vessels and vascular tissue. Although the majority of the figure drawings depict a forceps 10 for use in connection with endoscopic or laparoscopic surgical procedures, the present disclosure may be used for more traditional open surgical procedures. For the purposes herein, the forceps 10 is described in terms of an endoscopic or laparoscopic instrument; however, it is contemplated that an open version of the forceps may also include the same or similar operating components and features as described below.

Forceps 10 includes a shaft 12 that has a distal end 16 dimensioned to mechanically engage the end effector assembly 100 and a proximal end 14 that mechanically engages the housing 20. Details of how the shaft 12 connects to the end effector assembly 100 are described in more detail below. The proximal end 14 of shaft 12 is received within the housing 20 and the connections relating thereto are also described in detail below. In the drawings and in the descriptions that follow, the term "proximal", as is traditional, will refer to the end of the forceps 10 that is closer to the user, while the term "distal" will refer to the end that is farther from the user.

Forceps 10 also includes an electrosurgical cable 310 that may be internally divided into two or more leads which may connect the forceps 10 to a source of electrosurgical energy, e.g., a generator. Generators such as those sold by Covidien, located in Boulder, Colo. may be used as a source of both bipolar electrosurgical energy for sealing vessel and vascular tissues as well as monopolar electrosurgical energy which is typically employed to coagulate or cauterize tissue. It is envisioned that the generator may include various safety and performance features including isolated output, impedance control and/or independent activation of accessories.

Handle assembly 30 includes two movable handles 30a and 30b disposed on opposite sides of housing 20. Handles 30a and 30b are movable relative to one another to actuate the end effector assembly 100 as explained in more detail below with respect to the operation of the forceps 10.

Rotating assembly 80 is mechanically coupled to housing 20 and is rotatable approximately 90 degrees in either direction about a longitudinal axis "A." Rotating assembly 80, when rotated, rotates shaft 12, which, in turn, rotates end effector assembly 100. Such a configuration allows end effector assembly 100 to be rotated approximately 90 degrees in either direction with respect to housing 20.

Figure 6:
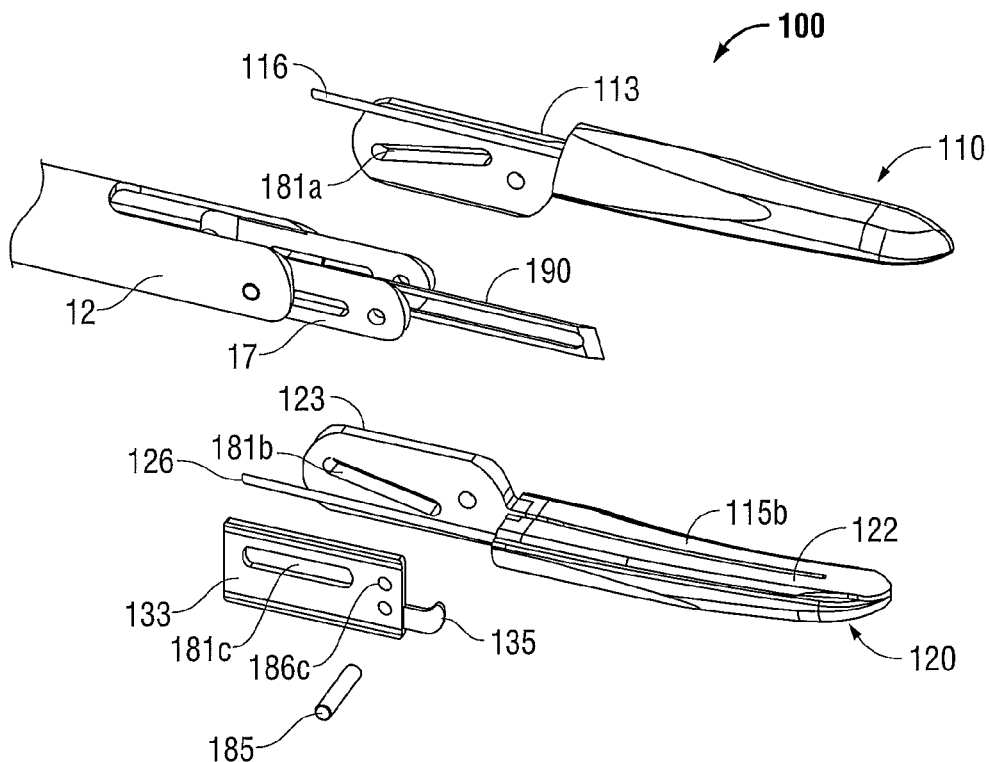
FIG. 6 is a partially exploded, perspective view of the end effector assembly.

As mentioned above, end effector assembly 100 is attached at the distal end 16 of shaft 12 and includes a pair of opposing jaw members 110 and 120 (see FIG. 6). Handles 30a and 30b of handle assembly 30 ultimately connect to drive assembly 60 (see FIG. 2A) which, together, mechanically cooperate to impart movement of the jaw members 110 and 120 from a first, open position wherein the jaw members 110 and 120 are disposed in spaced relation relative to one another, to a second, clamping or closed position wherein the jaw members 110 and 120 cooperate to grasp tissue therebetween.

Turning now to the more detailed features of the present disclosure as described with respect to FIGS. 1A-8, handles 30a and 30b each include an aperture 33a and 33b, respectively, defined therein which enables a user to grasp and move each respective handle 30a and 30b relative to one another. Handles 30a and 30b also include ergonomically-enhanced gripping elements 39a and 39b, respectively, disposed along an outer edge thereof which are designed to facilitate gripping of the handles 30a and 30b during activation. It is envisioned that gripping elements 39a and 39b may include one or more protuberances, scallops and/or ribs to enhance gripping.

As best illustrated in FIG. 1A, handles 30a and 30b are configured to extend outwardly on opposite sides from a transverse axis "B" defined through housing 20 which is perpendicular to longitudinal axis "A". Handles 30a and 30b are movable relative to one another in a direction parallel to axis "B" to open and close the jaw members 110 and 120 as needed during surgery. Details relating to the inner-working components of forceps 10 are disclosed in commonly-owned U.S. patent application Ser. No. 11/540,335. This forceps style is commonly referred to as an "in-line" or hemostat style forceps. In-line hemostats or forceps are more commonly manufactured for open surgical procedures and typically include a pair of shafts having integrally coupled handles which are movable relative to one another to open and close the jaw members disposed at the distal end thereof.

Figure 2A:
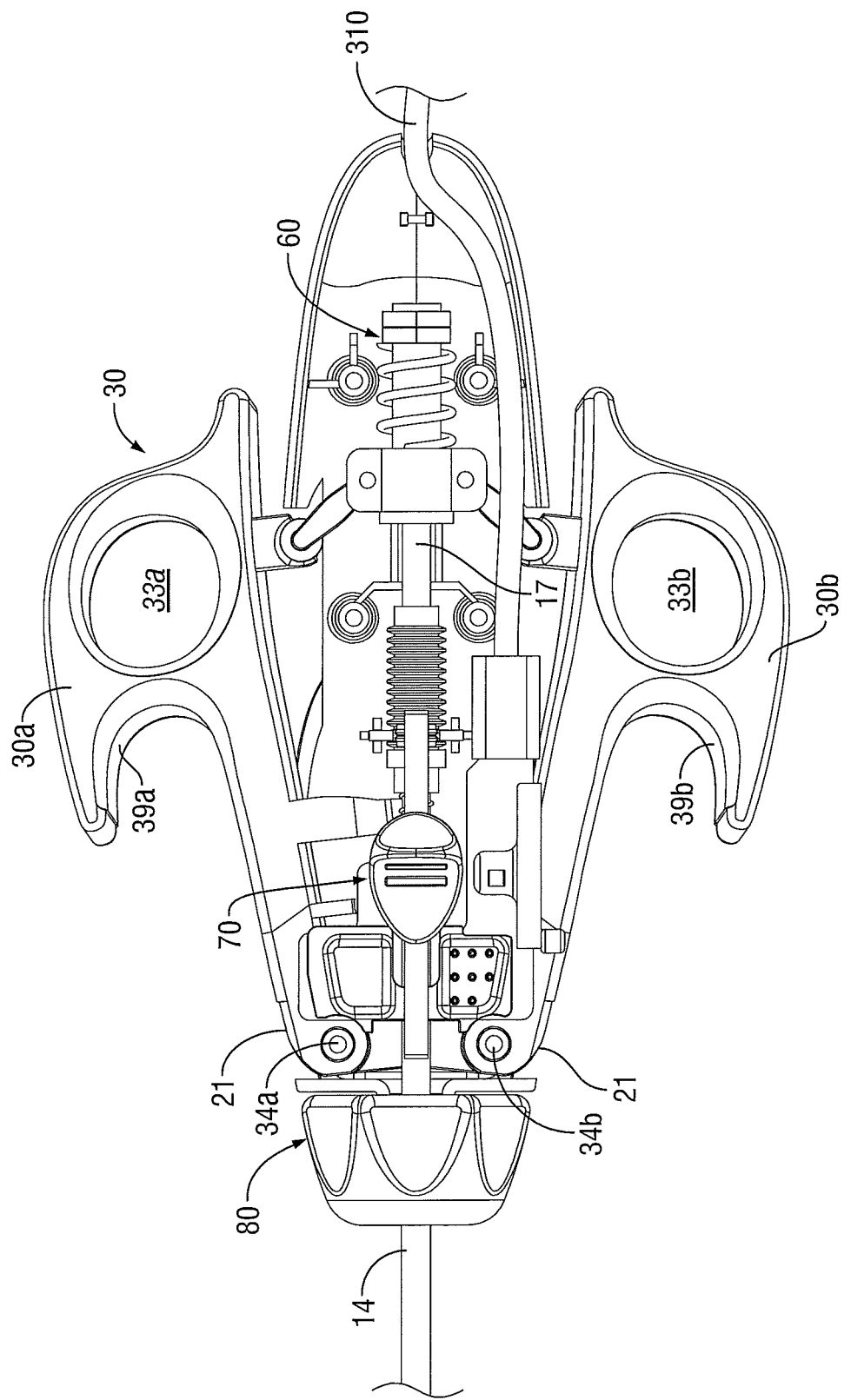
FIG. 2A is an enlarged, top view of the forceps of FIG. 1A showing the disposition of the internal components when the forceps is in an open configuration.
Figure 2B:
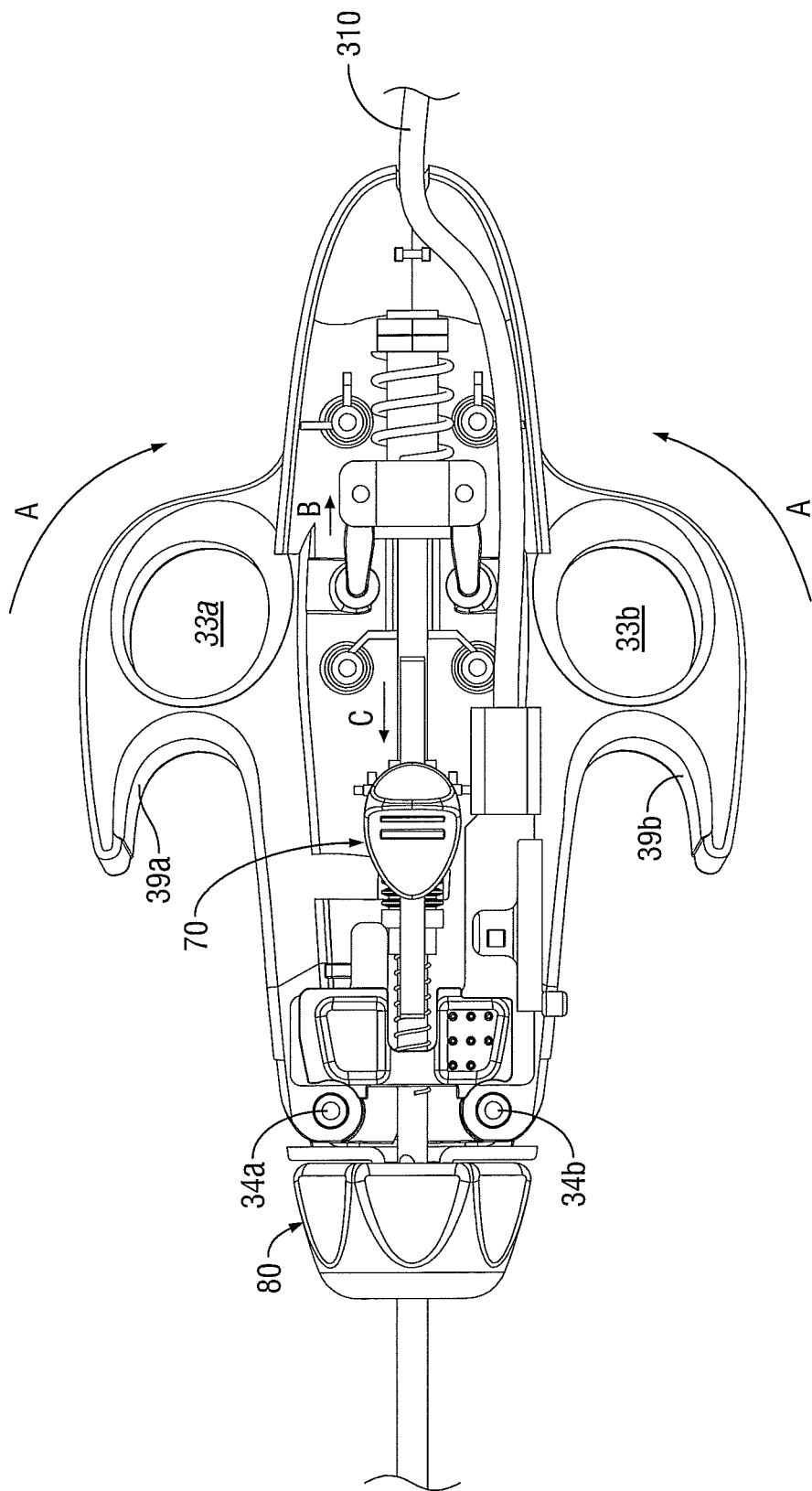
FIG. 2B is an enlarged, top view of the forceps of FIG. 1B showing the disposition of the internal components when the forceps is in a closed configuration.
Figure 3A:
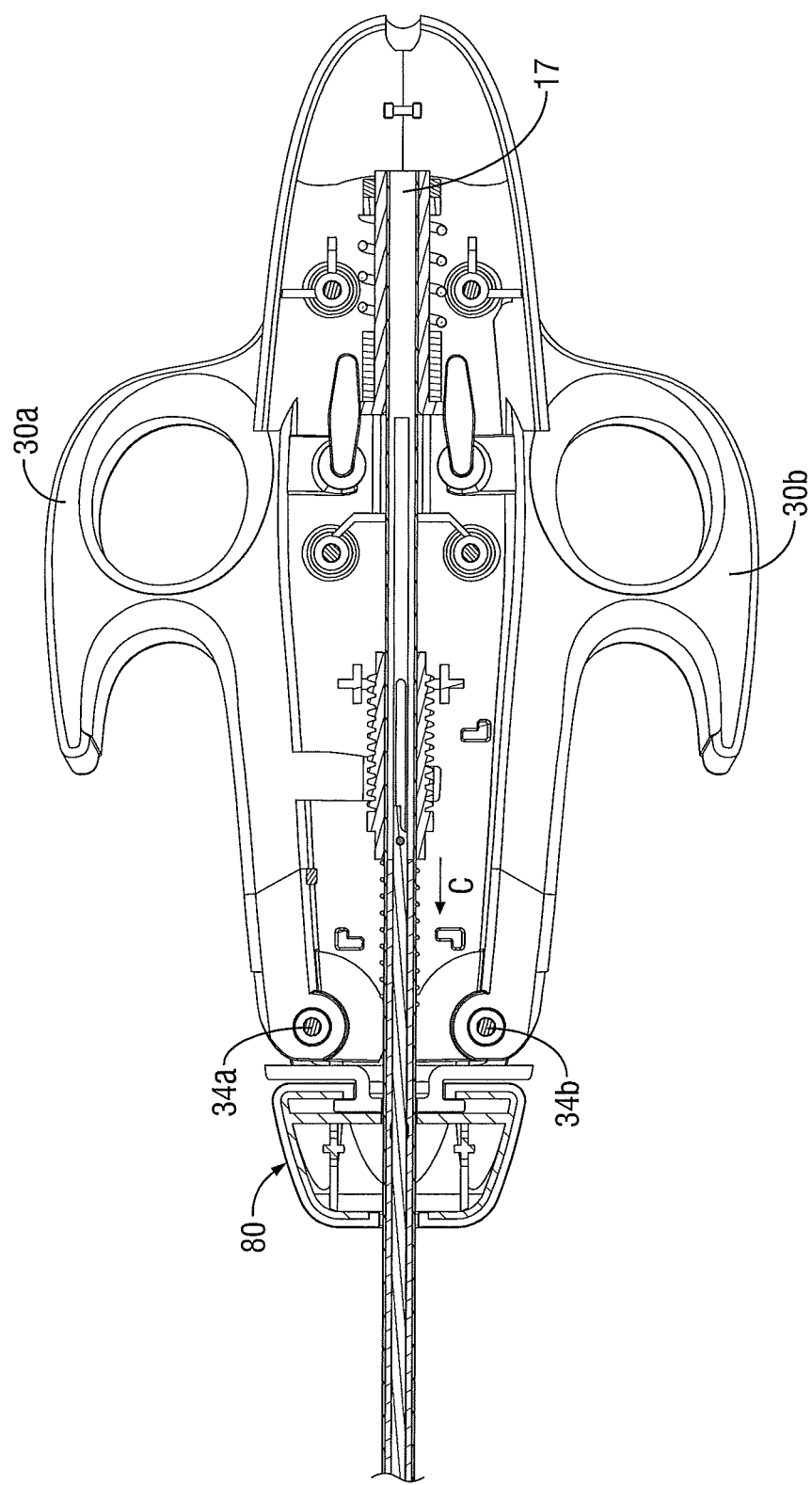
FIG. 3A is an enlarged, top view showing the knife actuator after actuation.
Figure 3B:
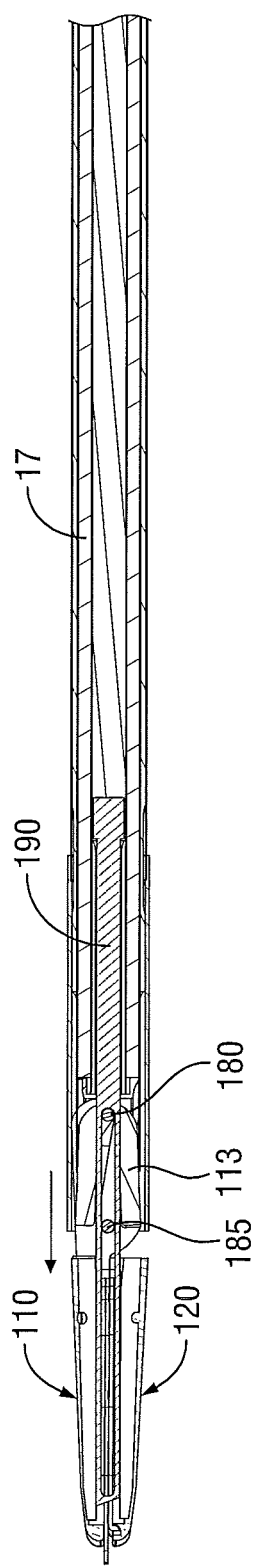
FIG. 3B is a greatly-enlarged, side cross sectional view of the end effector assembly showing the position of the knife after actuation.

As best seen in FIGS. 2A and 2B, the distal end of each handle 30a and 30b is selectively moveable about pivot pins 34a and 34b attached to a distal end 21 of the housing 20 to actuate the jaw members 110 and 120. Movement of the handles 30a and 30b away from one another (and the housing 20) unlocks and opens the handles 30a and 30b and, in turn, the jaw members 110 and 120 for subsequent grasping or re-grasping of tissue. In one embodiment, the handles 30a and 30b may be biased in an open configuration to facilitate handling and manipulation of the jaws within an operative field. Various spring-like mechanisms are contemplated which may be utilized to accomplish this purpose.

Movable handles 30a and 30b are designed to provide a distinct lever-like mechanical advantage over conventional handle assemblies. The enhanced mechanical advantage for actuating the jaw members 110 and 120 is gained by virtue of the unique position and combination of several inter-cooperating elements which reduce the overall user forces necessary to obtain and maintain the jaw members 110 and 120 under ideal operating pressures of about 3 kg/cm2 to about 16 kg/cm2. Details relating to the working components the handle assembly and drive assembly are disclosed in above-mentioned U.S. patent application Ser. No. 11/540,335. In other words, it is envisioned that the combination of these elements and their positions relative to one another enables the user to gain lever-like mechanical advantage to actuate the jaw members 110 and 120 enabling the user to close the jaw members 110 and 120 with lesser force while still generating the required forces necessary to effect a proper and effective tissue seal.

As shown best in FIGS. 4A, 4B, 5 and 6, the end effector assembly 100 is designed as a bilateral assembly, i.e., both jaw members 110 and 120 pivot relative to one another about a pivot pin 185 disposed therethrough. A unilateral end effector assembly is also envisioned. End effector assembly 100 further includes a knife guide 133 that houses the knife blade 190 for translation therethrough. Knife guide 133 is assembled with flanges 113 and 123 to allow pivotable movement of the flanges 113 and 123 about a pivot pin 185 disposed between the jaw members 110 and 120 upon translation of a drive pin 180 as explained in more detail below.

More particularly, jaw members 110 and 120 include proximal flanges 113 and 123, respectively, which each include an elongated angled slot 181a and 181b, respectively, defined therethrough. Drive pin 180 mounts jaw members 110 and 120 and knife guide 133 to the end of a rotating shaft 18 and within a cavity 17' defined at the distal ends 17a and 17b of drive actuator or sleeve 17 (See FIG. 5). Knife guide 133 includes an elongated slot 181c defined therethrough, configured for accepting the drive pin 180 and for allowing translation of the drive pin 180 within slots 181a-181c, which pivots the jaw members 110 and 120 relative to one another for grasping tissue. Knife guide 133 may also provide a unique safety feature for the forceps 10 as described in more detail below.

Upon actuation of the drive assembly 60, the drive sleeve 17 reciprocates which, in turn, causes the drive pin 180 to ride within slots 181a and 181b to open and close the jaw members 110 and 120 as desired and similarly causes the drive pin 180 to ride within slot 181c of knife guide 133. The jaw members 110 and 120, in turn, pivot about pivot pin 185 disposed through respective pivot holes 186a and 186b defined within flanges 113 and 123, the jaw members 110 and 120 and hole 186c disposed within knife guide 133. Upon actuation, knife guide 133 remains oriented in alignment with the shaft 12 as the jaws move about pivot pin 185 (See FIG. 6). As can be appreciated, squeezing handles 30a and 30b toward the housing 20 pulls drive sleeve 17 and drive pin 180 proximally to close the jaw members 110 and 120 about tissue grasped therebetween and pushing the sleeve 17 distally opens the jaw members 110 and 120 for grasping purposes.

Figure 7:
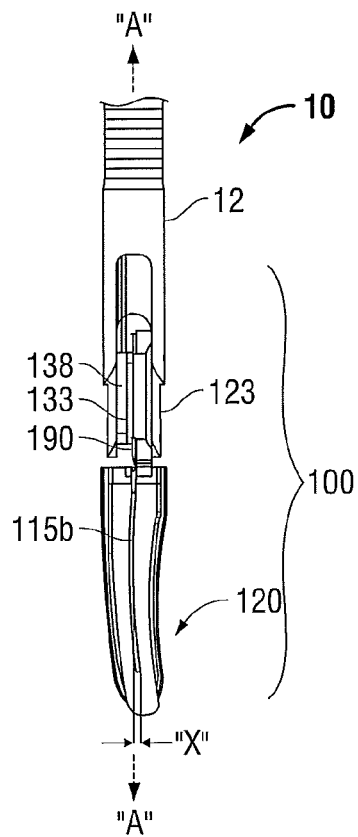
FIG. 7 is a top view of the end effector assembly with the upper jaw member removed.

Flanges 113 and 123 of jaw members 110 and 120, respectively, are positioned in an abutting relationship with one another and knife guide 133 is positioned adjacent to flanges 113 and 123. Flanges 113, 123 and knife guide 133 are assembled and engaged via pivot pin 185 disposed through apertures 186a, 186b, and 186c, respectively. Further, flanges 113, 123 are pivotable about one another via a drive pin 180 disposed through slots 181a and 181b of flanges 113,123, respectively. A knife path 138 may be defined between flange 113 and knife guide 133, as shown in FIGS. 6 and 7. The knife path 138 longitudinally aligns with knife channels 115a and 115b defined within jaw members 110 and 120, such that knife blade 190 travels in a substantially straight path through knife path 138 and, further, through knife channels 115a and 115b.

Alternatively, the orientation of flanges 113 and 123 may be reversed, with knife path 138 being defined between flange 123 and blade guide 133. In contrast to prior known designs, the abutting relationship between flanges 113 and 123 (in either orientation) strengthens the jaw flanges 113 and 123 since a blade path or blade channel does not need to be defined therebetween but, rather, is defined on an exterior side of one of the flanges 113 and 123. Thus, the knife 190 travels between the blade guide 133 and the flanges 113 and 123 and not between flanges. By manufacturing the knife path 138 on either side of the flanges 113 and 123, jaw splay may also be more easily controlled and tighter tolerances may be employed during the manufacturing process, thereby allowing tighter tolerances on certain features of the jaw member 110 and 120 resulting in better overall performance.

For example, the knife channels 115a and 115b defined within the jaw members 110 and 120, respectively, may be more precisely aligned with less splay between the jaw members 110 and 120, thereby facilitating knife blade 190 translation. Moreover, the strength of the flanges 113 and 123 is enhanced as well as the union therebetween, e.g., flat-on-flat abutting flange surfaces have more surface contact making the union therebetween stronger. The knife guide 133 may also be configured to pre-load jaw members 110 and 120 to help ensure proper alignment of knife channel halves 115a and 115b upon closing of the jaw members 110 and 120 as explained in more detail below.

As best shown in FIG. 6, blade guide 133 may include a blade stop or hook 135 disposed at a distal end thereof. The blade stop 135 may be integrally associated with the knife guide 133 (FIG. 6), the purpose of which is explained immediately below, or pivotably engaged with the knife guide 133, the purpose of which is explained with reference to FIG. 9. The relationship between flanges 113 and 123 and blade guide 133 is established by pivot pin 185 disposed through apertures 186a, 186b, and 186c, respectively, and by drive pin 180 disposed through slots 181a, 181b and 181c, respectively. Accordingly, when jaw members 110, 120 are in a first, or open, position, knife guide 133 pivots such the blade stop 135 interferes with the knife path 138, thereby preventing distal translation of knife blade 190. In one embodiment, this may be accomplished by the knife guide 133 including an elongated slot 181c that is cammed when the drive pin 180 is biased in a distal-most position such that the knife guide 133 and blade stop 135 pivot thereby obstructing the knife path 138.

When handles 30a and 30b are squeezed toward the housing 20, drive sleeve 17 and drive pin 180 are pulled proximally to close the jaw members 110 and 120, which also pivots the knife guide 133 so that the blade stop 135 no longer obstructs or interferes with the knife path 138. Thus, in this embodiment, the knife guide 133, by virtue of the blade stop 135, prevents distal advancement of knife blade 190 when jaw members 110 and 120 are in the first, open position and permits distal advancement of knife blade 190 when jaw members 110 and 120 are in the second, closed position.

Alternatively, a hook (not shown) may be disposed on either of flanges 113 or 123. The hook would operate in substantially the same manner as the blade stop 135 disposed on the blade guide 133 in the embodiment discussed above. Accordingly, as jaw members 110, 120 are opened, the hook on flange 113 or 123 is pivoted into the path of knife blade 190, thereby preventing distal translation of knife blade 190. When handles 30a and 30b are squeezed toward the housing 20, drive sleeve 17 and drive pin 180 are pulled proximally to close the jaw members 110 and 120. The pulling of drive pin 180 also pivots flanges 113 and 123, thereby closing the jaw members 110 and 120 and as a result, the hook is pivoted out of the path of knife blade 190.

Figure 4A:
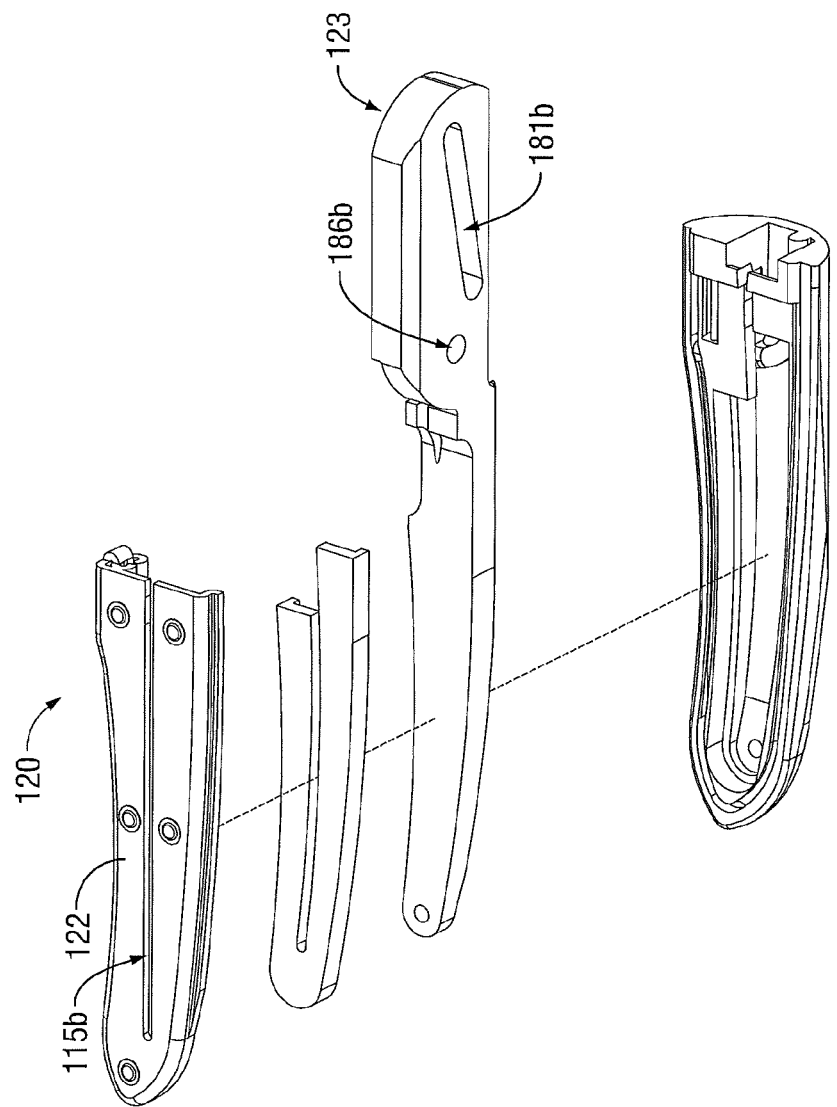
FIG. 4A is a greatly-enlarged, perspective view of the bottom jaw of the end effector assembly with parts separated.
Figure 4B:
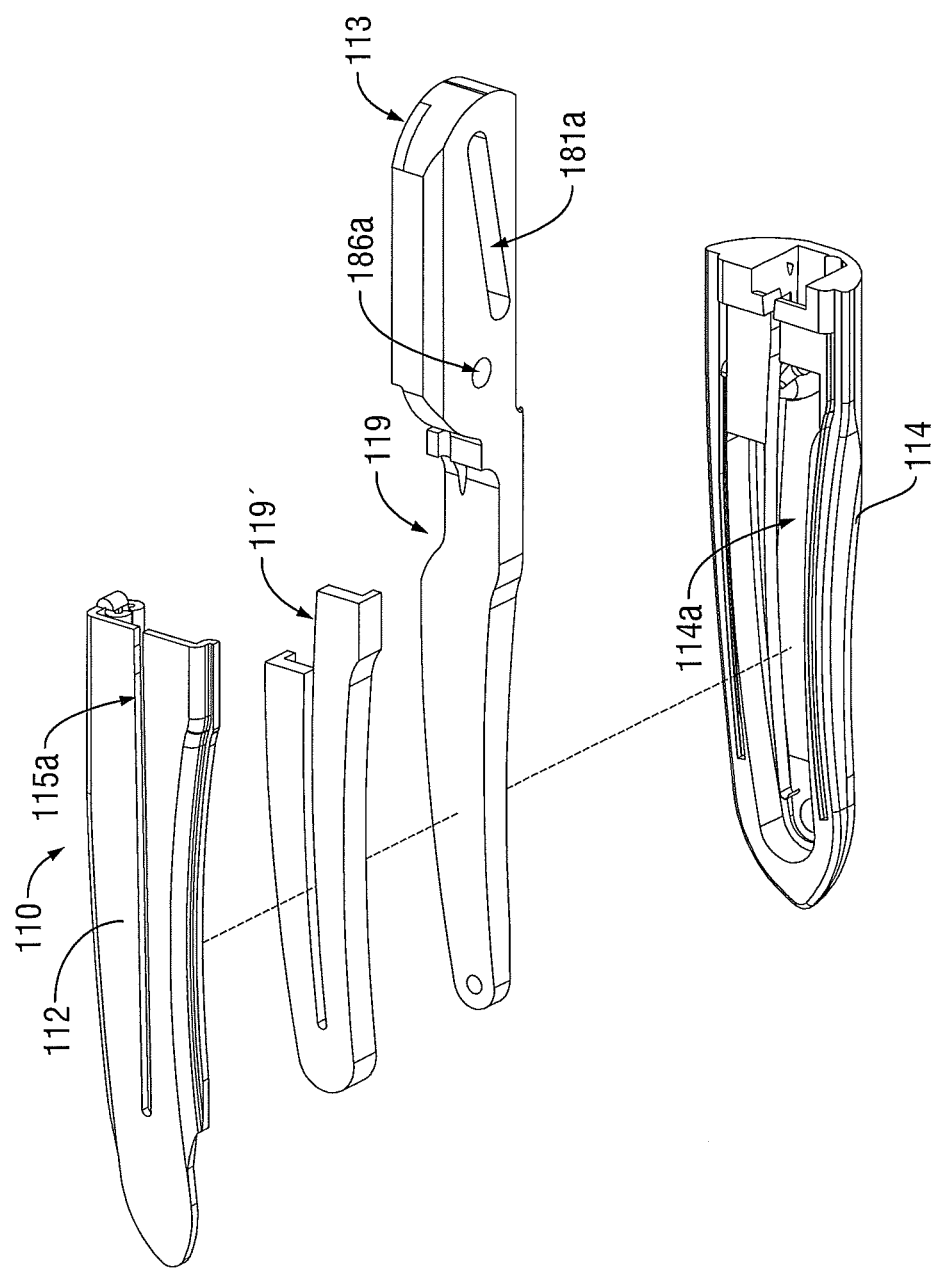
FIG. 4B is a greatly-enlarged, perspective view of the top jaw of the end effector assembly with parts separated.
Figure 5:
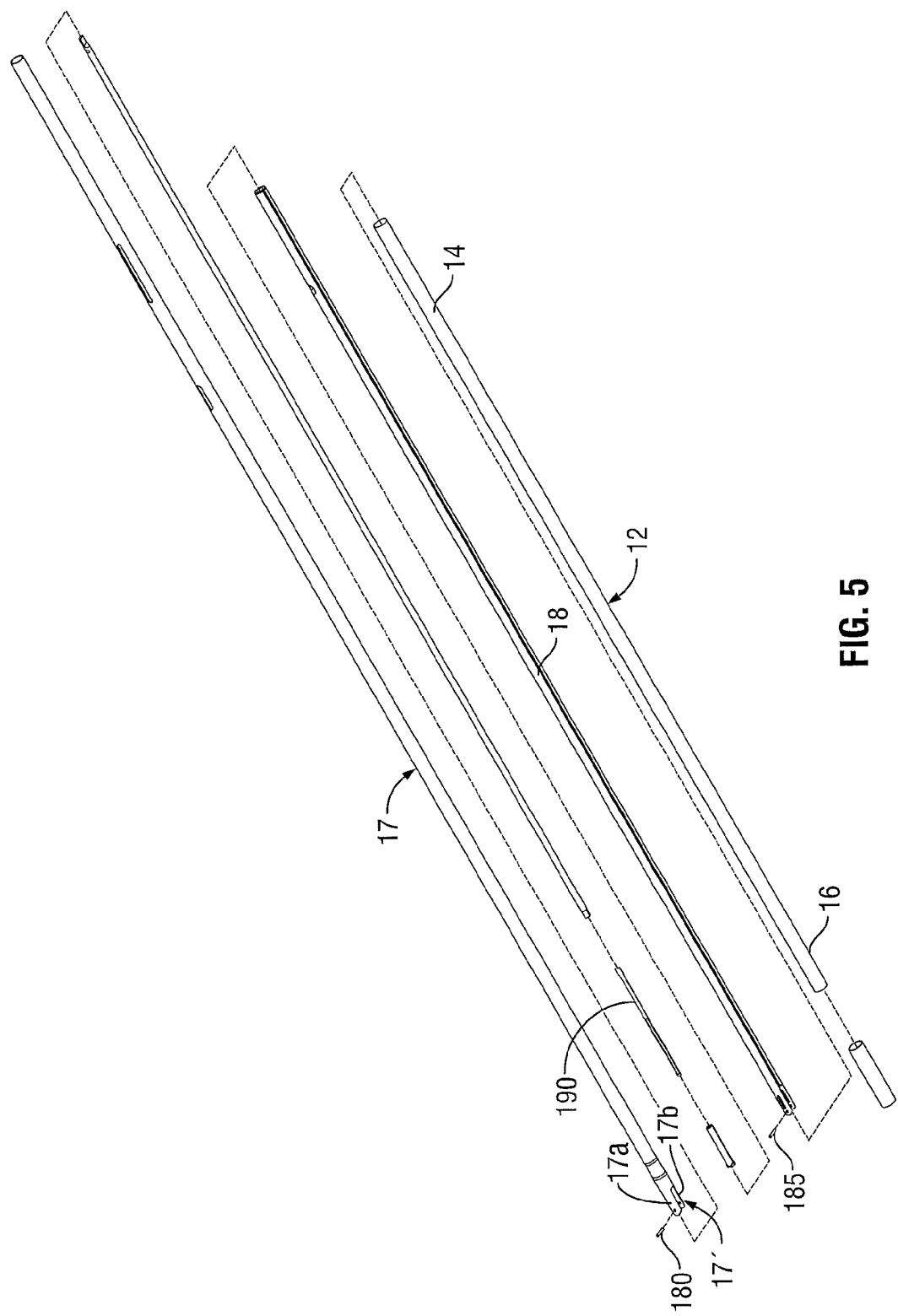
FIG. 5 is a greatly-enlarged, perspective view of the elongated shaft for housing various moving parts of the drive assembly and knife assembly.

As best shown in FIG. 4B, jaw member 110 also includes a support base 119 that extends distally from flange 113 and that is configured to support an insulative plate 119' thereon. Insulative plate 119', in turn, is configured to support an electrically conductive tissue engaging surface or sealing plate 112 thereon. Sealing plate 112 may be affixed atop the insulative plate 119' and support base 119 in any suitable manner, e.g., snap-fit, over-molding, stamping, ultrasonically welded, etc. Support base 119 together with the insulative plate 119' and electrically conductive tissue engaging surface 112 are encapsulated by an outer insulative housing 114. Outer housing 114 includes a cavity 114a that is dimensioned to securely engage the electrically conductive sealing surface 112 as well as the support base 119 and insulative plate 119'. This may be accomplished by stamping, by overmolding, by overmolding a stamped electrically conductive sealing plate and/or by overmolding a metal injection molded seal plate. All of these manufacturing techniques produce jaw member 110 having an electrically conductive surface 112 that is substantially surrounded by an insulating substrate 114.

The electrically conductive surface or sealing plate 112 and the outer housing 114, when assembled, form longitudinally-oriented knife channel 115a defined therethrough for reciprocation of the knife blade 190. It is envisioned that the knife channel 115a cooperates with corresponding knife channel 115b defined in jaw member 120 to facilitate longitudinal extension of the knife blade 190 along a preferred cutting plane to effectively and accurately separate the tissue along the formed tissue seal. As discussed above, when knife blade 190 is deployed, at least a portion of knife blade 190 advances through knife path 138 and into knife channels 115a and 115b. In addition to the blade stop 135, handle 30a may includes a lockout flange (not shown) which prevents actuation of the knife assembly 70 when the handle 30a is open thus preventing accidental or premature activation of the knife blade 190 through the tissue. A more detailed discussion of the lockout flange is discussed in above-mentioned U.S. patent application Ser. No. 11/540,335.

As explained above and as illustrated in FIGS. 4A and 4B, in one embodiment, the knife channel 115 is formed when the jaw members 110 and 120 are closed. In other words, the knife channel 115 includes two knife channel halves—knife channel half 115a disposed in sealing plate 112 of jaw member 110 and knife channel half 115b disposed sealing plate 122 of jaw member 120. It is envisioned that the knife channel 115 may be configured as a straight slot with no degree of curvature which, in turn, causes the blade 190 to move through the tissue in a substantially straight fashion. Alternatively, and as shown, the knife channel 115 may be curved, which has certain surgical advantages. In the particular embodiment shown in FIGS. 6 and 7, the knife channel 115 (knife channel 115a shown) is curved and is offset from the centerline or longitudinal axis "A" of the forceps 10 by a distance "X" (See FIGS. 7 and 8). This offset distance "X" may be in the range of about 0.010 inches to about 0.040 inches.

The offset orientation of the knife blade 190 (by virtue or the knife guide 133 being assembled on one side of the flanges 113 and 123 allows the knife blade to enter the knife channel 115 in a substantially straight orientation thereby facilitating separation of tissue. Moreover, the knife blade 190 travels in a substantially straight manner through most of the knife channel 115 and is only forced to bend around the knife channel 115 towards a distal end of the jaw members 110 and 120. Further, the offset orientation of the knife channel, e.g., knife channel 115b, and the disposition of the knife blade 190 traveling through the knife guide 133 also enhances the cutting effect and reduces the chances of the knife blade 190 binding during translation (extension or retraction).

As mentioned above, when the jaw members 110 and 120 are closed about tissue, knife channels 115a and 115b form a complete knife channel 115 to allow longitudinal extension of the knife blade 190, from the knife path 138, in a distal fashion to sever tissue along a tissue seal. Knife channel 115 may be completely disposed in one of the two jaw members, e.g., jaw member 120, depending upon a particular purpose. It is also envisioned that jaw member 120 may be assembled in a similar manner as described above with respect to jaw member 110.

Figure 8:
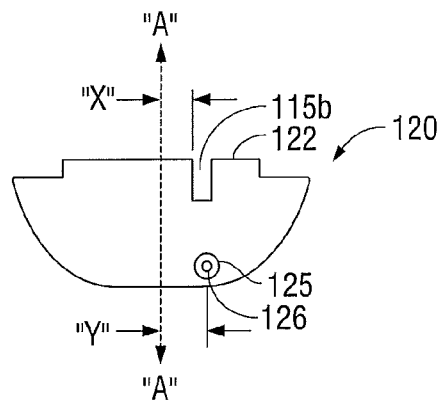
FIG. 8 is a rear, perspective view of one of the jaw members in accordance with an alternate embodiment of the present disclosure.

Referring now to FIGS. 6 and 8, electrical lead or wire 126 is shown extending from shaft 12 through knife housing 133 and entering wire tube 125 of jaw members 120. Wires 116 and 126 are used to supply electrical energy to electrically conductive sealing surfaces 112 and 122 of jaw members 110 and 120, respectively. In the embodiment of FIG. 6, knife housing 133 also acts as a wire guide, configured to guide wires 116 and 126 to jaw members 110 and 120. Electrical leads or wires 116 and 126 are protected by knife housing 133. Wire tube 125 (FIG. 8) of jaw member 120, may be offset from a longitudinal axis "Y" of the forceps 10 in the same direction as the offset knife channel 115b, such that knife channel 115b is disposed above the wire tube 125. The offset "X" of the knife channel, e.g., knife channel 115b, and the offset "Y" of the disposition of the electrical lead or wire 126 relative to longitudinal axis "A" may be different or the same depending upon a particular purpose or to facilitate manufacturing. For example, as mentioned above, the offset distance "X" may be in the range of about 0.010 inches to about 0.040 inches whereas the offset distance "Y" may be in the range about 0.040 inches to about 0.140 inches. In addition, particular "X" and "Y" configurations may be as follows: When "X" is about 0.010 inches "Y" may be about 0.040 inches; when "X" is about 0.017 inches "Y" may be about 0.070 inches; and when "X" is about 0.034 inches "Y" may be about 0.140 inches. Other configurations and offsets for "X" and "Y" are also contemplated and within the scope of this disclosure.

Referring now to FIGS. 9-12, one embodiment of an end effector assembly 400 for use with forceps 10 includes a pair of jaw members 402, 404, a knife assembly 410, and a cam assembly 420.

One or both jaw members 402, 404 are moveable relative to the other about a pivot 440 operably associated with the forceps 10. One or both jaw members 402, 404 are moveable between an open position (FIGS. 9-11) and a closed position (FIG. 12) for grasping tissue. One or both of the jaw members 402, 404 include a knife channel 406 defined therein that extends therealong. One or both of the jaw members 402, 404 may be adapted to connect to an electrosurgical energy source to electrosurgically treat tissue.

The knife assembly 410 includes a knife blade 412 and an actuation shaft 414. The knife blade 412 may be affixed to a distal end of the actuation shaft 414. The actuation shaft 414 is operably associated with the knife trigger assembly 70 of forceps 10 (FIG. 1). The knife blade 412 is disposed distally relative to the pivot 440. The actuation shaft 414 is configured for slidable translation through the pivot 440 to allow selective advancement of the knife blade 412 through the knife channel 406 upon activation by the knife trigger assembly 70.

The cam assembly 420 is operably coupled to each moveable jaw member 402, 404 and is actuatable to move one or both jaw members 402, 404 between the open and the closed position for grasping tissue therebetween. The cam assembly 420 includes an actuator clevis 422 operably coupled to a support clevis 430 operably associated with the housing 20. The cam assembly 420 is configured to move one or both jaw members 402, 404 between the open and the closed position upon selective longitudinal translation thereof. The actuator clevis 422 may be moveable via an actuator tube 450 operably associated with the shaft 12 extending from the housing 20 to actuate both jaw members 402, 404.

Figure 9:
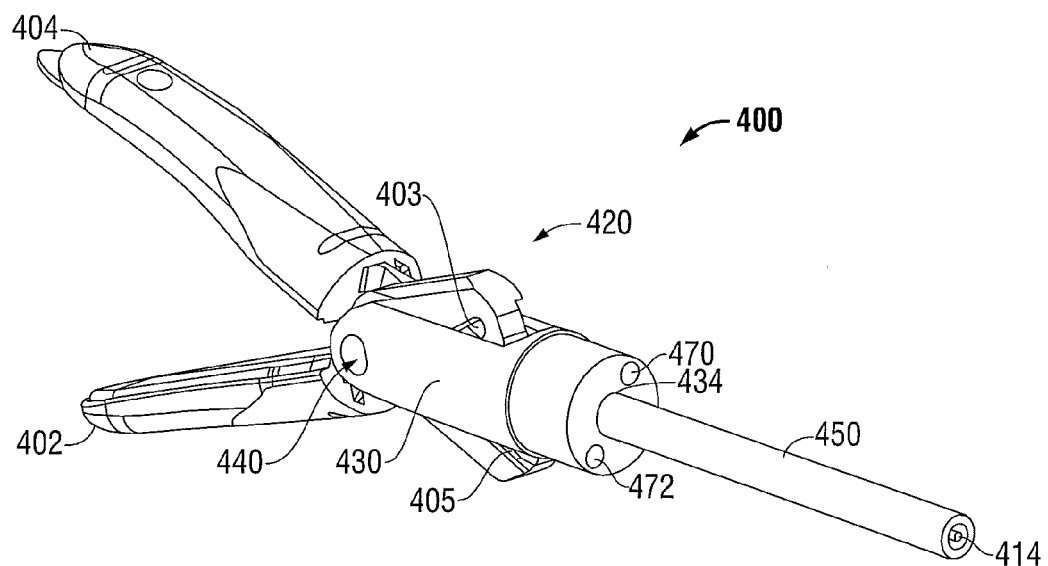
FIG. 9 is right, rear, perspective view of an end effector assembly shown in a first position according to one embodiment of the present disclosure.
Figure 10:
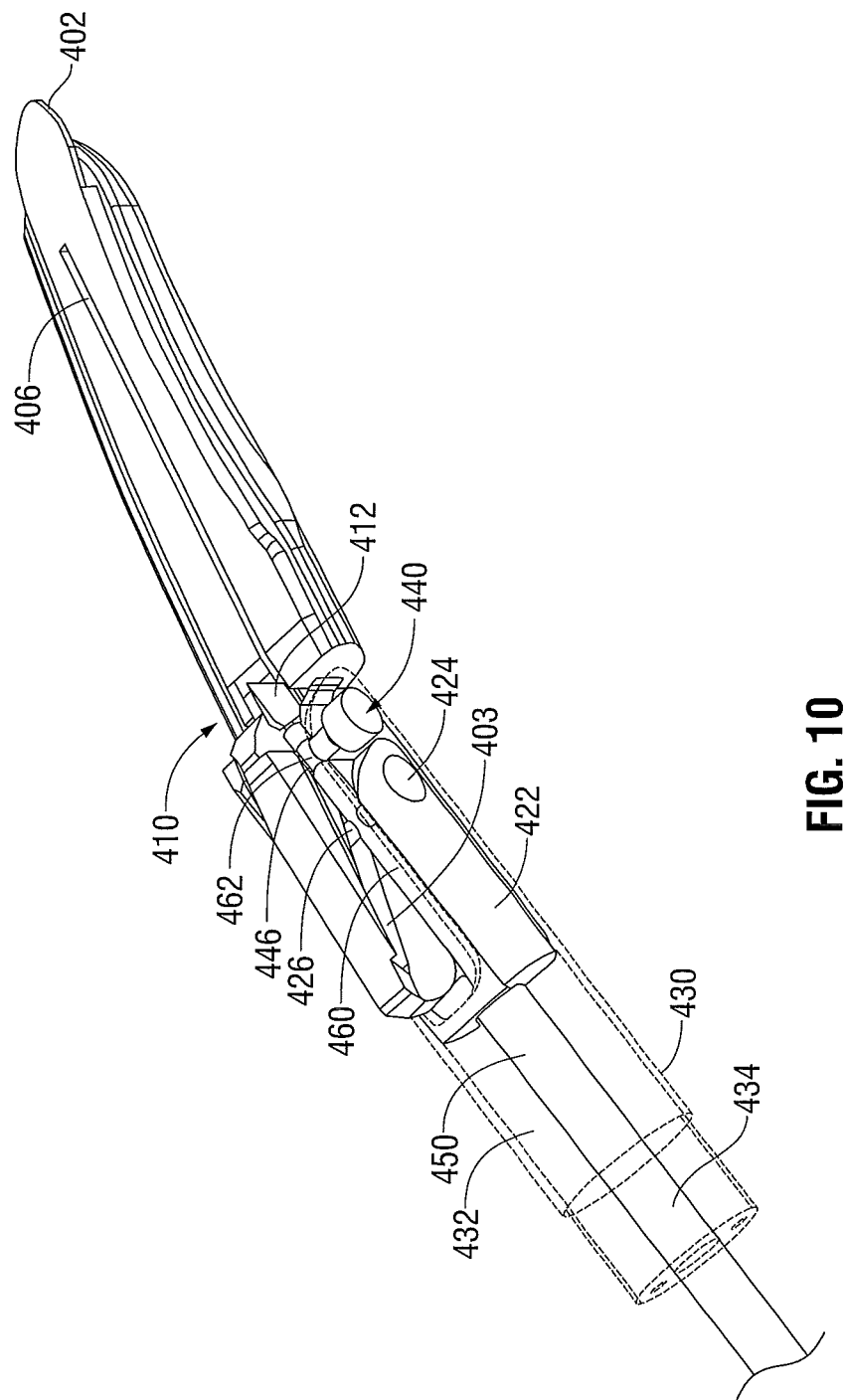
FIG. 10 is a left, perspective view of the end effector assembly of FIG. 9 with the top jaw thereof removed for clarity and with a clevis thereof shown in phantom.

The pair of jaw members 402, 404 are mounted to the support clevis 430 about the pivot 440. The support clevis 430 defines an actuator bore 432 and an actuator tube bore 434 for facilitating the slidable translation of the actuator clevis 422 and the actuator tube 450 therethrough. With reference to FIG. 9, cable channels 470, 472, etc. may also be defined through support clevis 430 for receiving one or more of the leads of the electrosurgical cable 310 (FIG. 1) therethrough.

The pivot 440 has first and second sections 442, 444 defining a passage 446 therebetween configured to permit the actuation shaft 414 to slidably translate therethrough. In some embodiments, the first and second sections 442, 444 of the pivot 440 are fixedly connected to the support clevis 430. The support clevis 430 is mounted to the distal end of the actuator tube 450. The actuator tube 450 is operably associated with the drive assembly 60 for longitudinally translating the actuator tube 450. The actuator tube 450 is configured to slidingly receive the knife assembly 410 therein.

The actuator clevis 422 includes one or more cam pins 424, 426 extending therefrom. One or both jaw members 402, 404 define one or more cam slots 403, 405 therein such that the one or more cam slots 403, 405 and the one or more cam pins 424, 426 are configured to cooperate with one another to move each moveable jaw member 402, 404. The actuator tube 450 is configured to longitudinally translate the actuator clevis 422 and permit the slidable translation of the actuation shaft 414 therethrough for facilitating the translation of the knife blade 412. The actuator tube 450 slidably translates along a knife tube 460 mounted to the pivot 440 between the first and second sections 442, 444.

Figure 11:
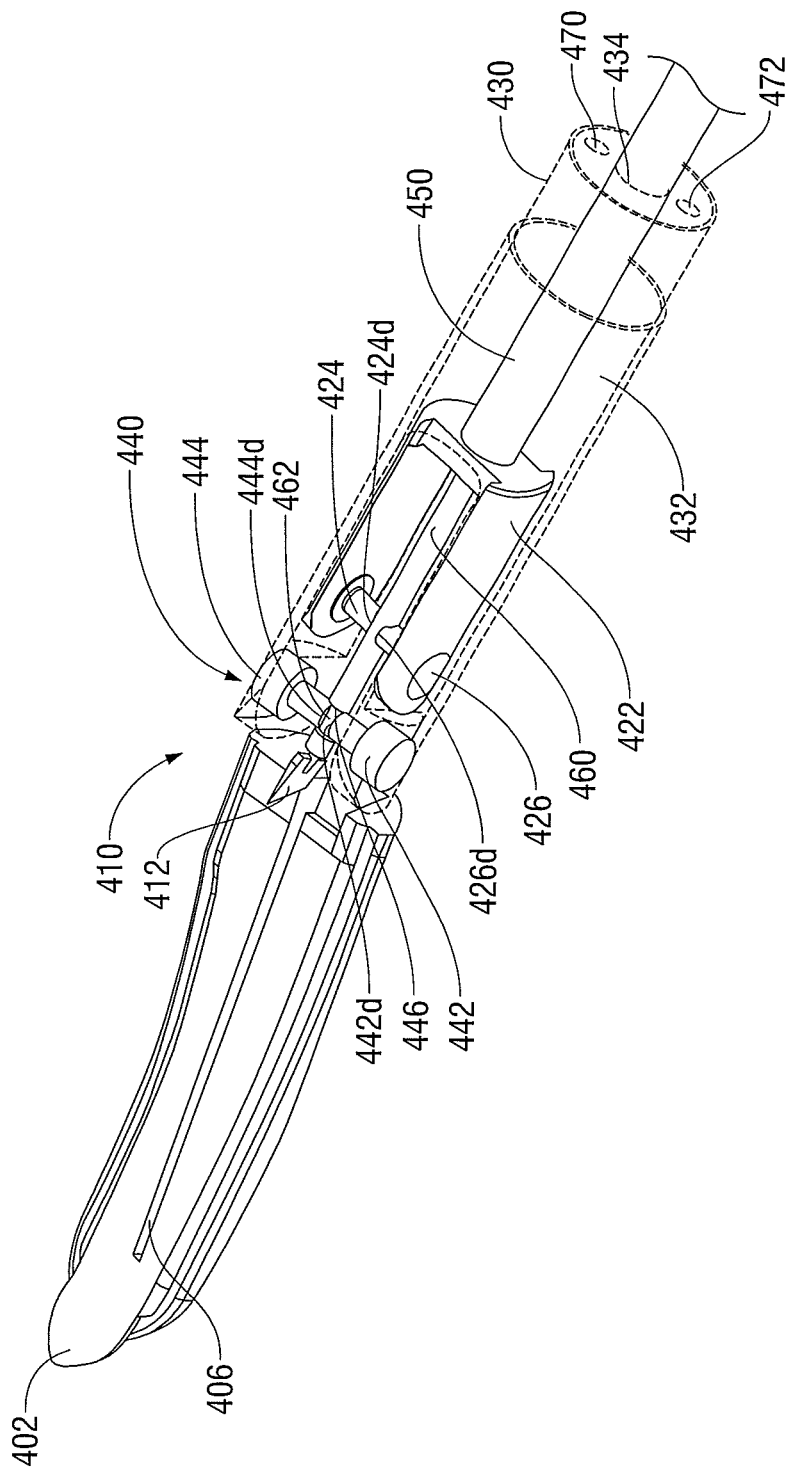
FIG. 11 is a right, perspective view of FIG. 10 with a proximal portion of the bottom jaw removed for clarity.
Figure 12:
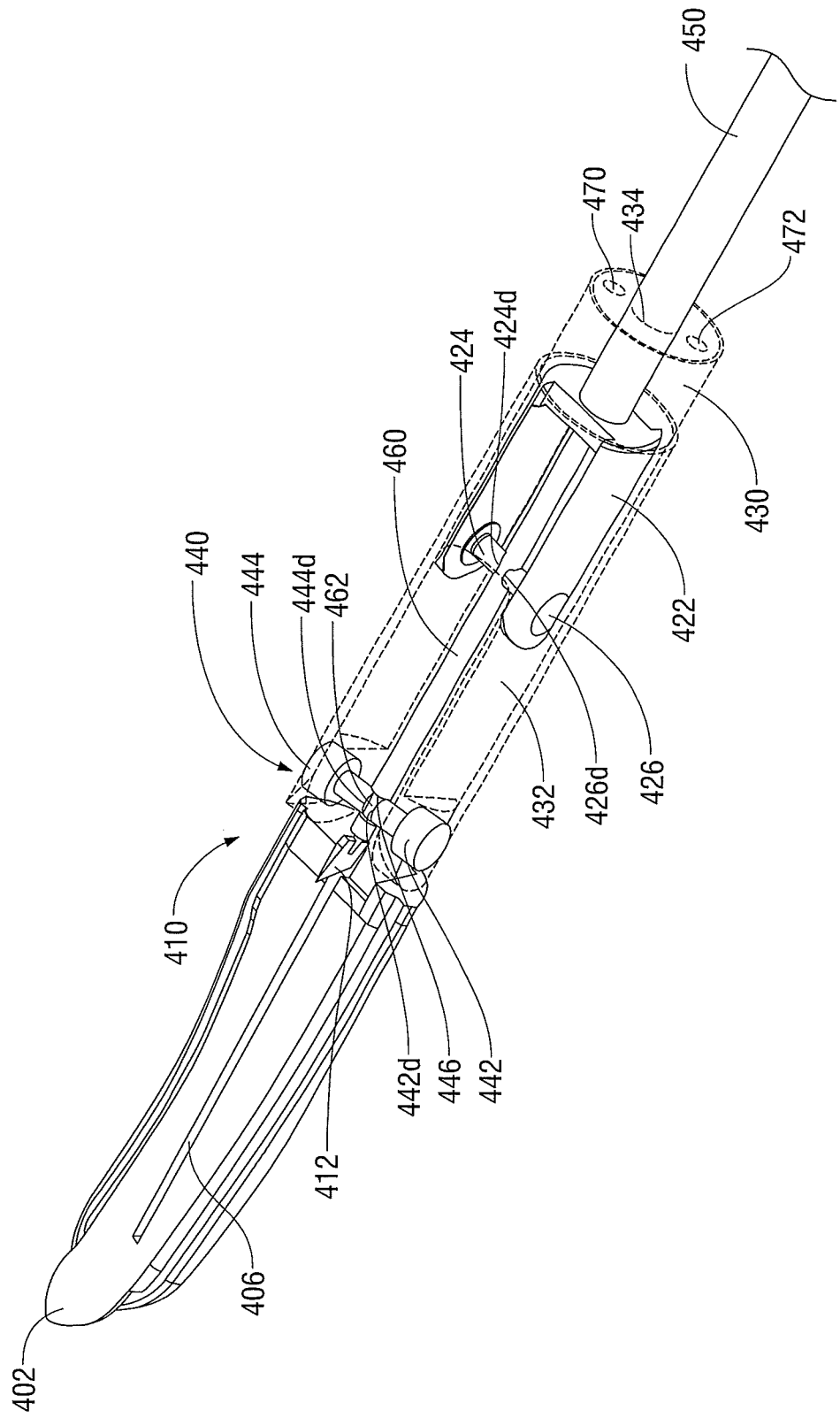
FIG. 12 is a right, perspective view of FIG. 11 illustrating a second position of the end effector assembly of FIG. 9.

The one or more cam pins 424, 426 are configured to slidably engage the knife tube 460 upon the selective longitudinal translation of the actuator clevis 422. The distal ends 424d, 426d of the cam pins 424, 426 are configured to slidably engage the outer surface of the knife tube 460. As illustrated in FIGS. 11 and 12, the distal ends 424d, 426d of the cam pins 424, 426 define a pin profile that may be generally crescent-shaped for cooperating with the generally circularly-shaped outer surface of the knife tube 460. The knife tube 460 and the pin profiles may have any suitable cross-sectional shape (e.g., circular or non-circular). The knife tube 460 defines a recess 462 adapted to mount each of the first and second sections 442, 444 of the pivot 440 at the distal ends 442d, 444d thereof. The distal ends 442d, 444d of each of the first and second sections 442, 444 define a profile configured to fixedly engage the recess 462. The profiles of both the distal ends 442d, 444d of the first and second sections 442, 444 define the passage 446 between each section 442, 444 for engaging the recess 462 of the knife tube 460. The passage 446 and the recess 462 may define any suitable cross-sectional shape (e.g., circular or non-circular). As illustrated in the embodiment of FIG. 11, the profiles of the first and second sections 442, 444 are each generally crescent-shaped to fixedly engage the circumferential groove that defines the recess 462 so that first and second sections 442, 444 provide a stationary pivot about which jaw members 402, 404 move.

In operation, upon actuation of the movable handles 30a and 30b, the drive assembly 60 slidably longitudinally translates the actuator tube 450 through the actuator tube bore 434 of the support clevis 430. The translation of the actuator tube 450 effectuates the longitudinal translation of the actuator clevis 422 through the actuator bore 432 of the support clevis 430. As the actuator clevis 422 translates, each cam pin 424, 426 slides within each respective cam slot 403, 405 and along the outer surface of the knife tube 460. When each cam pin 424, 426 translates through each respective cam slot 403, 405, the jaw members 402, 404 translate between the first position and the second position. In effect, each respective jaw member 402, 404 rotates about the pivot 440 in response to the longitudinal translation of the actuator clevis 422. Upon actuation of the knife trigger assembly 70, the actuation shaft 414 translates through the actuator tube 450 and the knife tube 460 such that the knife blade 412 is advanced through the knife channel 406 of the jaw members 402, 404.

Figure 13:
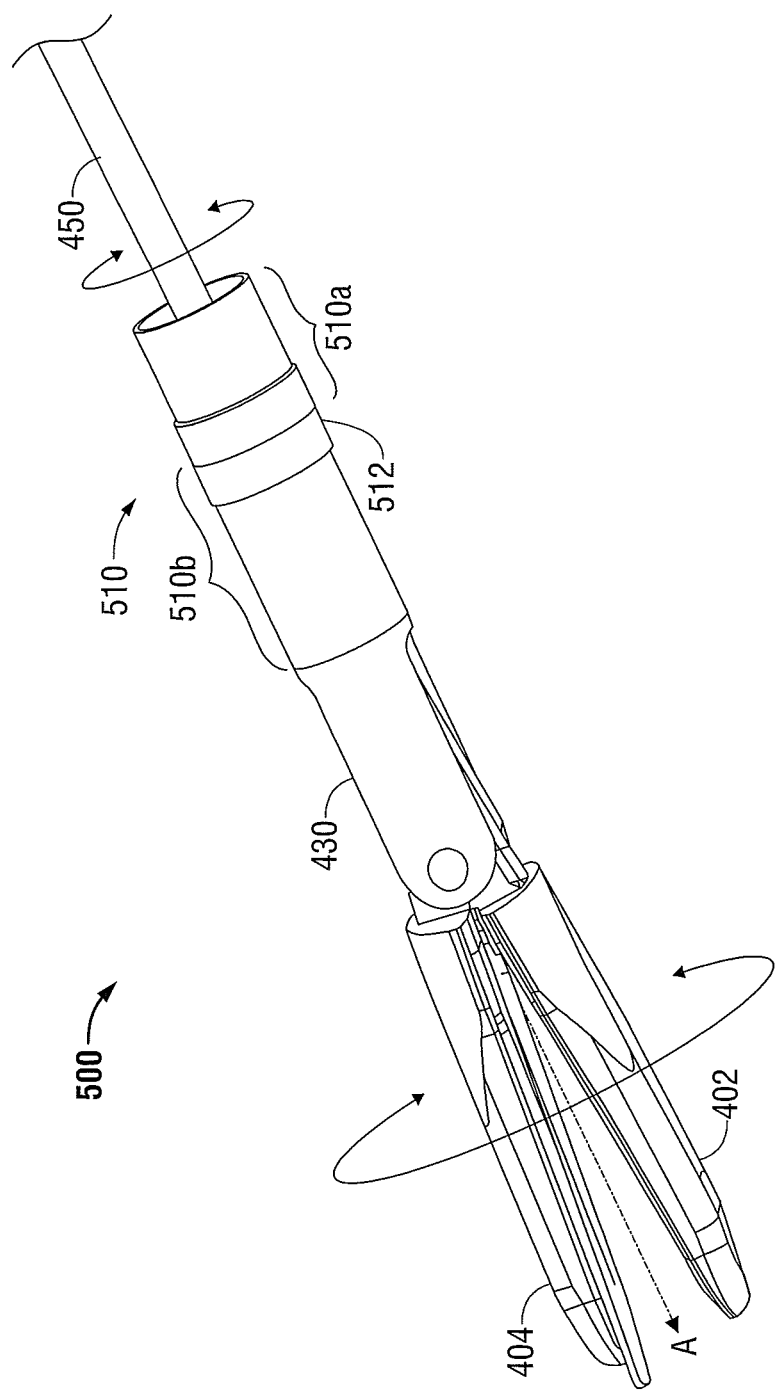
FIG. 13 is a right, perspective view of one embodiment of an end effector assembly.

With reference to FIG. 13, one embodiment of an end effector assembly 500 for use with forceps 10 includes a roll joint 510 secured to the distal end of the support clevis 430 and operably coupled to the actuator tube 450 for facilitating the rotational movement of the jaw members 402, 404. The roll joint 510 includes a stationary portion 510a and rotatable portion 510b. The stationary portion 510a is fixedly coupled to the handle assembly 30. The rotatable portion 510b is operably coupled to the stationary portion 510a and the actuator tube 450. The rotatable portion 510b includes one or more moveable interfaces 512 (e.g., one or more bearings, bushings, etc.) secured thereto. Each movable interface 512 is configured to permit relative rotation between the stationary portion 510a and the rotatable portion 510b.

In operation, the actuator tube 450 is rotated which, in turn, rotates the rotatable portion 510b in response thereto. With the actuator tube 450 fixedly mounted to the rotatable portion 510b and radially movable within the stationary portion 510a, the actuator tube 450 transmits torque to the jaw members 402, 404 via the roll joint 510 upon the rotational movement of the actuator tube 450. In this manner, the jaw members 402, 404 may be radially rotated about the longitudinal axis "A" while the handle assembly 30 remains stationary.

With these embodiments, the distance to the pivot point is significantly reduced which facilitates assembly and ease of use. In certain embodiments, this shortened distance to the pivot point facilitates articulation of the end effector.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly comprising:
a pair of jaw members, at least one of the pair of jaw members moveable about a pivot between an open position and a closed position relative to the other jaw member for grasping tissue, the pivot including first and second sections and defining a passage between the first and second sections;
a knife blade supported between the pair of jaw members distal to the pivot and coupled to an actuation shaft, the actuation shaft slidably translatable through the passage of the pivot to advance the knife blade;
a cam pin coupled to at least one of the pair of jaw members to move the at least one jaw member upon selective longitudinal translation of the cam pin through a cam slot defined in at least one of the pair of jaw members; and
a knife tube mounted to the pivot, the cam pin slidably engaged with the knife tube, the first and second sections of the pivot being engageable with a recess defined by the knife tube.

2. The end effector assembly according to claim 1, further comprising a trigger assembly configured to enable slidable translation of the actuation shaft upon actuation of the trigger assembly.

3. The end effector assembly according to claim 2, wherein the cam pin is secured to a movable actuator clevis configured to longitudinally translate the cam pin.

4. The end effector assembly according to claim 2, further including a roll joint operably coupled to a support clevis configured to receive the pair of jaw members, the roll joint facilitating rotational movement of the pair of jaw members about a longitudinal axis defined between proximal and distal ends of the pair of jaw members.

5. The end effector assembly according to claim 1, wherein at least one of the jaw members is adapted to connect to an electrosurgical energy source to electrosurgically treat tissue.

6. The end effector assembly according to claim 1, wherein the knife blade is affixed to a distal end of the actuation shaft.

7. A forceps, comprising:
a housing having a shaft that extends therefrom, the shaft including a support clevis at a distal end thereof;
a pair of jaw members mounted to the support clevis about a pivot, at least one jaw member moveable relative to the other about the pivot between an open position and a closed position for grasping tissue, the pivot having first and second sections defining a passage therebetween;
a knife blade disposed distally relative to the pivot;
an actuation shaft secured to the knife blade and configured for slidable translation through the passage defined between the first and second sections of the pivot to allow selective advancement of the knife blade;
an actuator clevis including at least one cam pin extending therefrom, at least one of the pair of jaw members defining at least one cam slot configured to slidably receive the at least one cam pin to move the at least one moveable jaw member, the longitudinal translation of the actuator clevis moving the at least one movable jaw member between the open position and the closed position; and
a knife tube supporting the actuation shaft and defining a recess adapted to receive the ends of the first and second sections of the pivot, the at least one cam pin configured to slide along an outer surface of the knife tube upon longitudinal translation of the actuator clevis.

8. The forceps according to claim 7, further including a roll joint operably coupled to the support clevis to facilitate rotational movement of the pair of jaw members.

9. The forceps according to claim 7, wherein at least one of the jaw members is adapted to connect to an electrosurgical energy source to electrosurgically treat tissue.

10. The forceps according to claim 7, wherein the knife blade is affixed to a distal end of the actuation shaft.

* * * * *